United States Patent [19]
Brosnahan et al.

[11] Patent Number: 6,123,728
[45] Date of Patent: Sep. 26, 2000

[54] MOBILE BEARING KNEE PROSTHESIS

[75] Inventors: Robert Brosnahan, Germantown; Albert Pothier, Memphis, both of Tenn.

[73] Assignee: Smith & Nephew, Inc., Memphis, Tenn.

[21] Appl. No.: 09/082,179

[22] Filed: May 20, 1998

Related U.S. Application Data

[60] Provisional application No. 60/059,131, Sep. 17, 1997.

[51] Int. Cl.⁷ .................................................... A61F 2/38
[52] U.S. Cl. ................................. 623/20.24; 623/20.14
[58] Field of Search .................................. 623/20, 18, 16

[56] References Cited

U.S. PATENT DOCUMENTS

| | | | |
|---|---|---|---|
| 4,016,606 | 4/1977 | Murray et al. | 623/20 |
| 4,094,017 | 6/1978 | Mattews et al. | 623/20 |
| 4,216,549 | 8/1980 | Hillberry et al. | 623/20 |
| 4,224,697 | 9/1980 | Murray et al. | 623/20 |
| 4,340,978 | 7/1982 | Buechel et al. | 623/20 |
| 4,673,407 | 6/1987 | Martin | 623/20 |
| 5,007,933 | 4/1991 | Sidebotham et al. | 623/20 |
| 5,032,132 | 7/1991 | Matsen, III et al. | 623/19 |
| 5,071,438 | 12/1991 | Jones et al. | 633/20 |
| 5,116,375 | 5/1992 | Hofmann | 623/20 |
| 5,314,483 | 5/1994 | Wehrli et al. | 623/20 |
| 5,370,699 | 12/1994 | Hood et al. | 623/20 |
| 5,395,401 | 3/1995 | Bahler | 623/20 |
| 5,404,398 | 4/1995 | Buford, III et al. | 623/20 |
| 5,549,686 | 8/1996 | Johnson et al. | 623/20 |
| 5,609,693 | 3/1997 | Walker | 623/20 |
| 5,702,466 | 12/1997 | Pappas et al. | 623/20 |
| 5,782,925 | 7/1998 | Collazo et al. | 623/20 |
| 5,871,543 | 2/1999 | Hofmann | 623/20 |
| 5,871,545 | 2/1999 | Goodfellow et al. | 623/20 |
| 5,935,173 | 8/1999 | Roger et al. | 623/20 |

FOREIGN PATENT DOCUMENTS

| | | | |
|---|---|---|---|
| 0 186 471 | 7/1986 | European Pat. Off. . | |
| 4985586 | 8/1992 | European Pat. Off. | 623/20 |
| 636353 | 2/1995 | European Pat. Off. | 623/20 |
| 2672798 | 8/1992 | France | 623/20 |
| 2698265 | 5/1994 | France | 623/20 |
| 43 08 563 | 9/1994 | Germany . | |
| 2219942 | 12/1989 | United Kingdom . | |
| 95 17860 | 7/1995 | WIPO . | |
| 96 24311 | 8/1996 | WIPO . | |

*Primary Examiner*—Paul J. Hirsch
*Assistant Examiner*—Michael B. Priddy
*Attorney, Agent, or Firm*—Garvey, Smith, Nehrbass & Doody, LLC

[57] ABSTRACT

A mobile bearing knee prosthesis enables a surgeon to convert a mobile bearing insert having articular surfaces, supported by a tibial base plate or tray from a rotating and translating prosthesis to one that rotates only. This conversion is accomplished with a fastener or locking member that connects through an opening in the insert to the tibial base plate. This prosthesis can be used as part of a total knee surgery when the surgeon chooses to use a prosthesis that incorporates a movable articular surface.

20 Claims, 13 Drawing Sheets

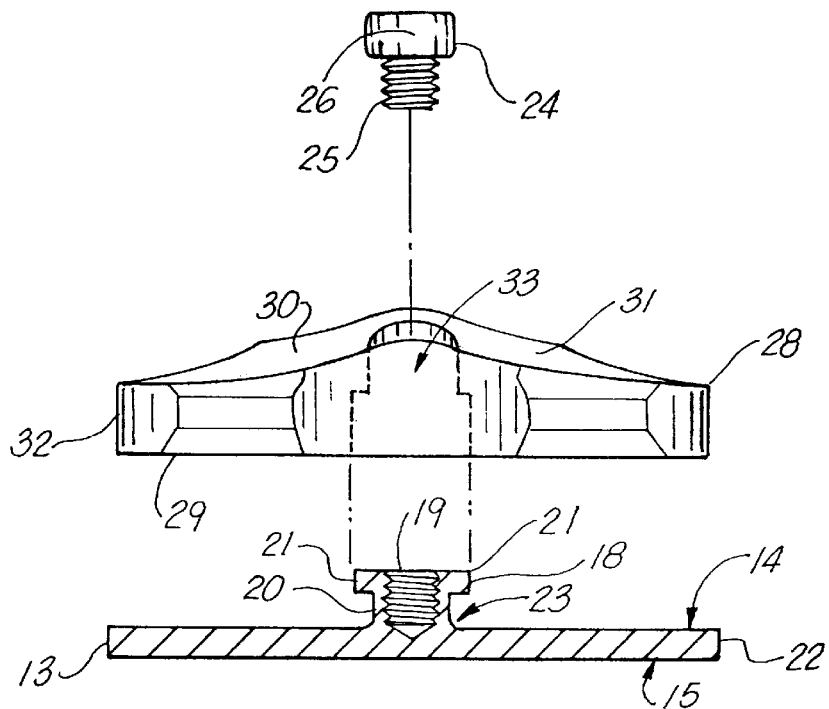
FIG. 5
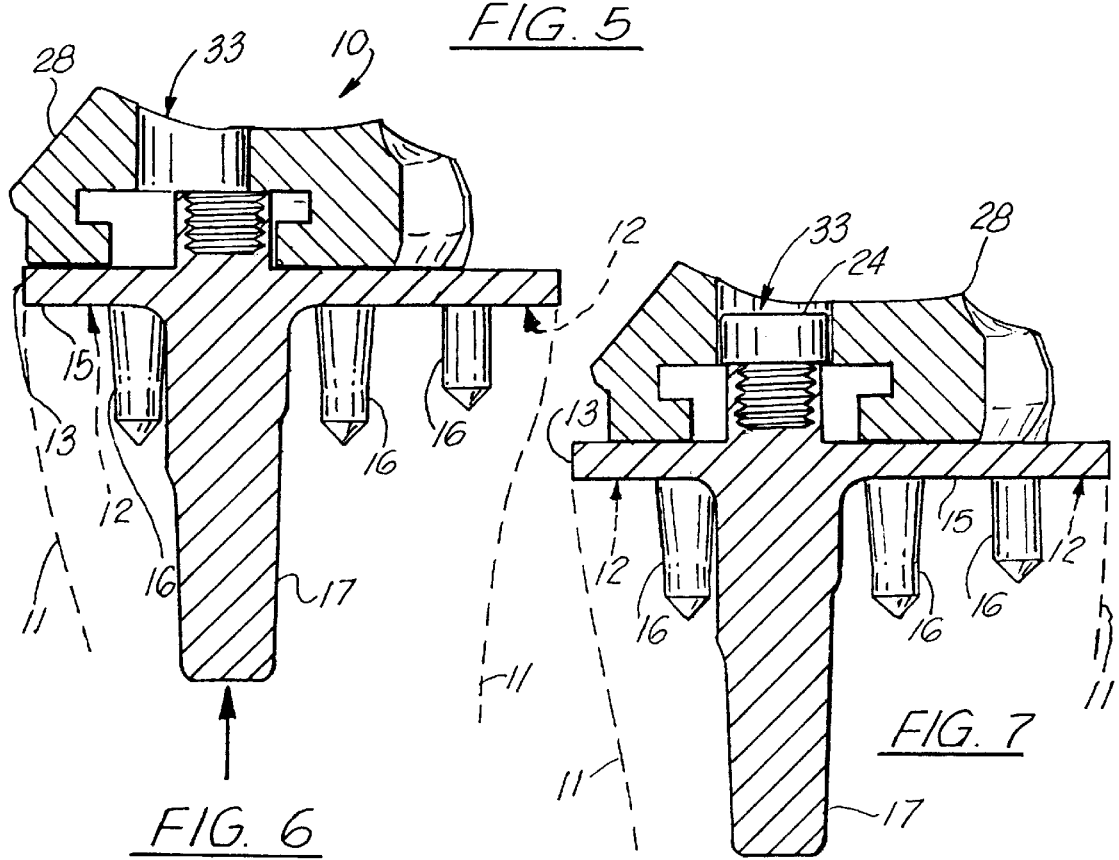
FIG. 6
FIG. 7

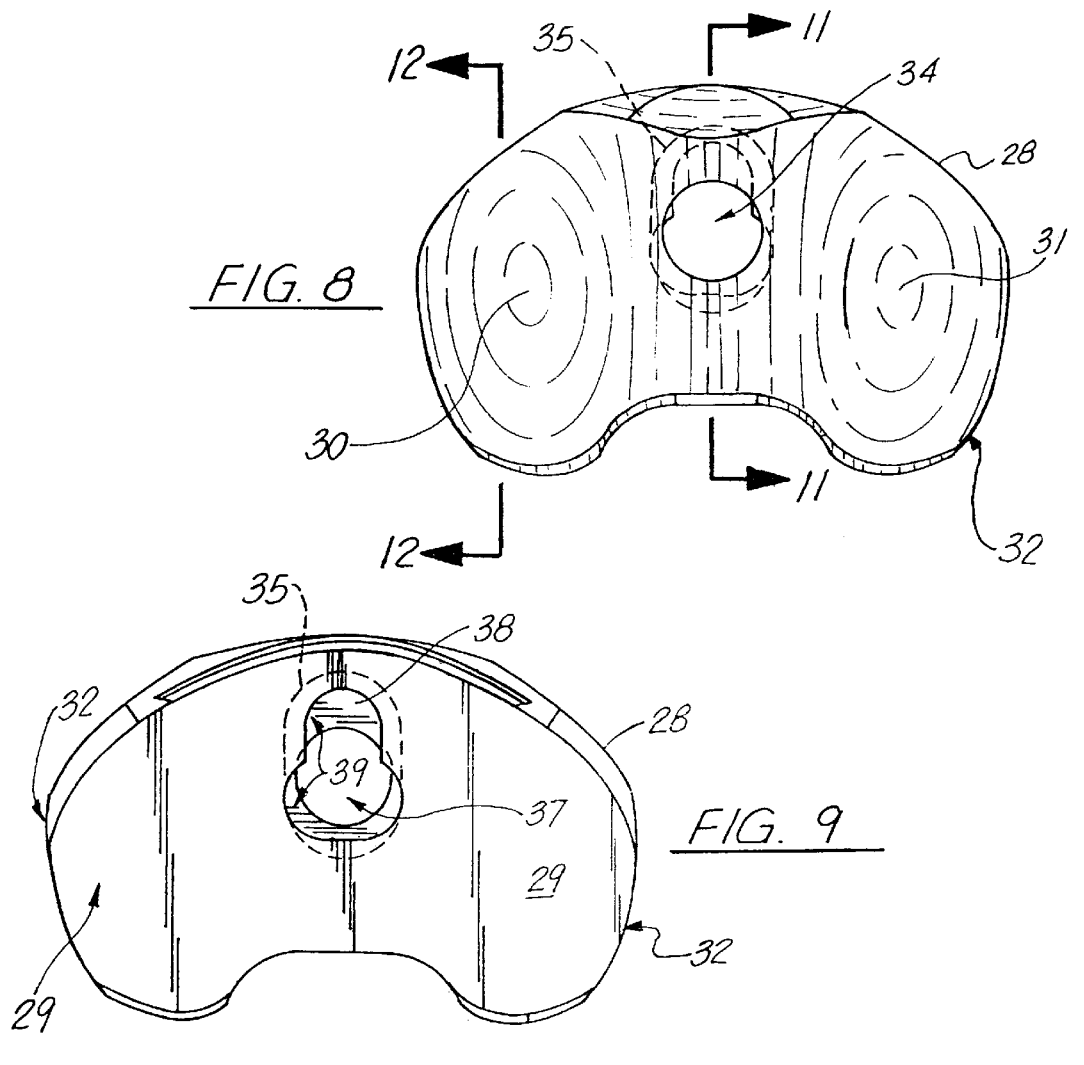
FIG. 8
FIG. 9
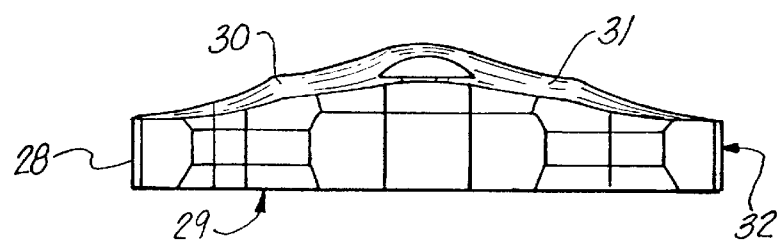
FIG. 10
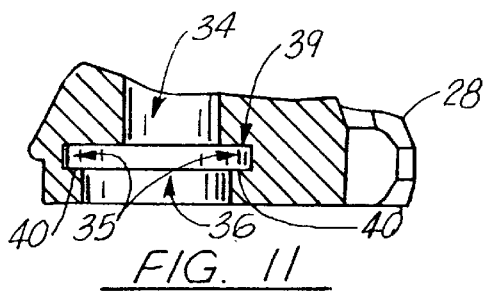
FIG. 11
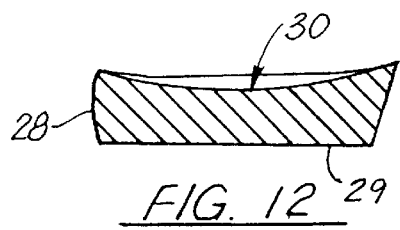
FIG. 12

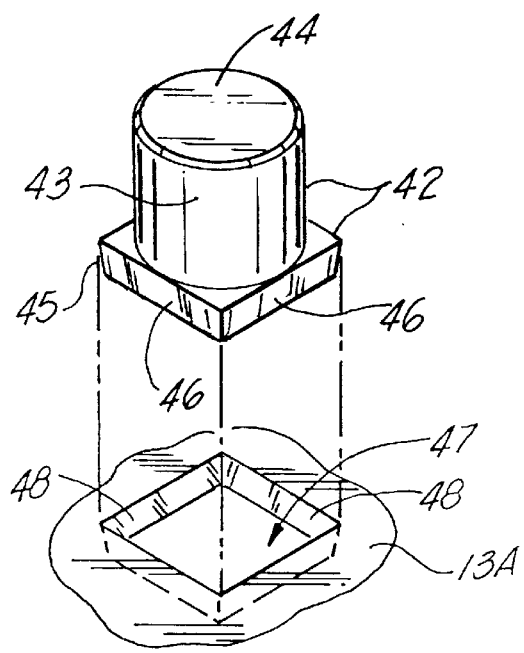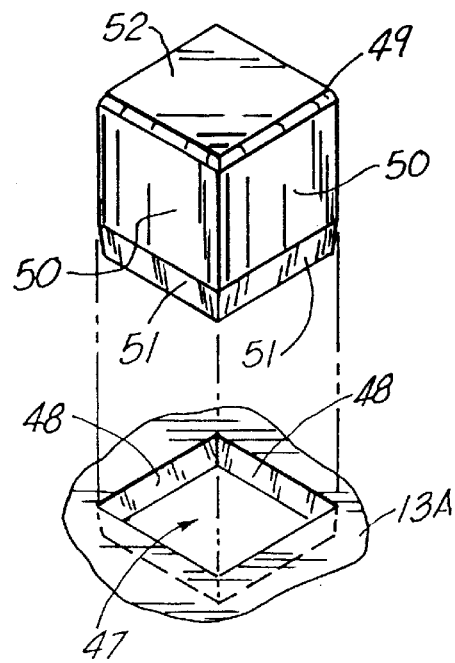
FIG. 18  FIG. 19
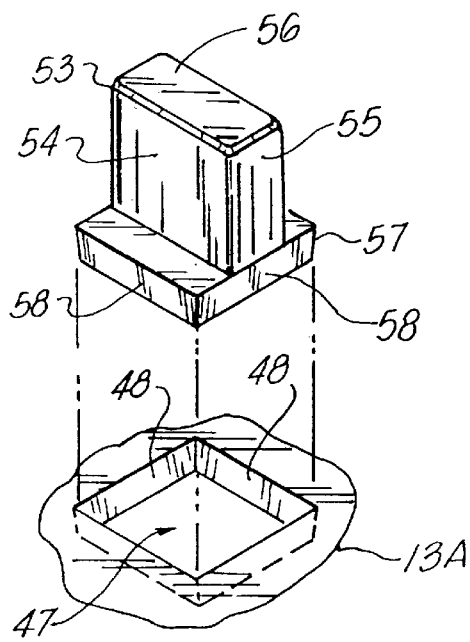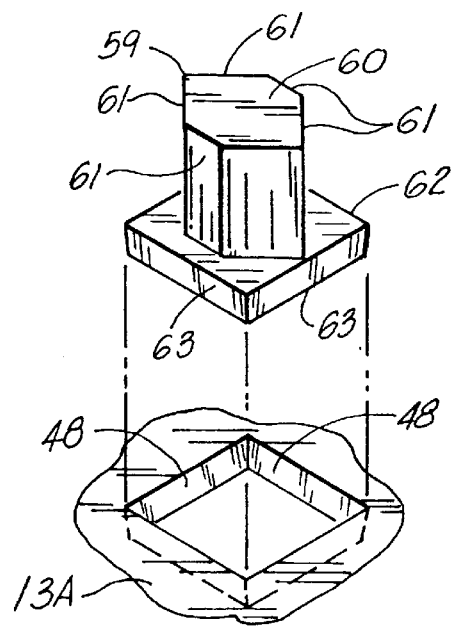
FIG. 20  FIG. 21

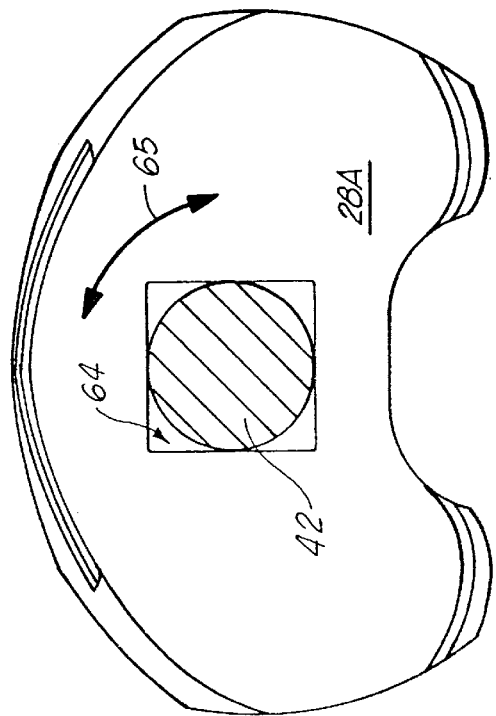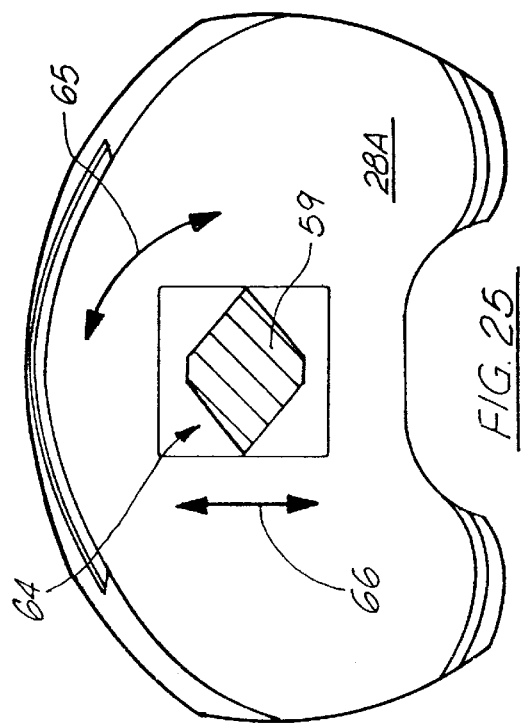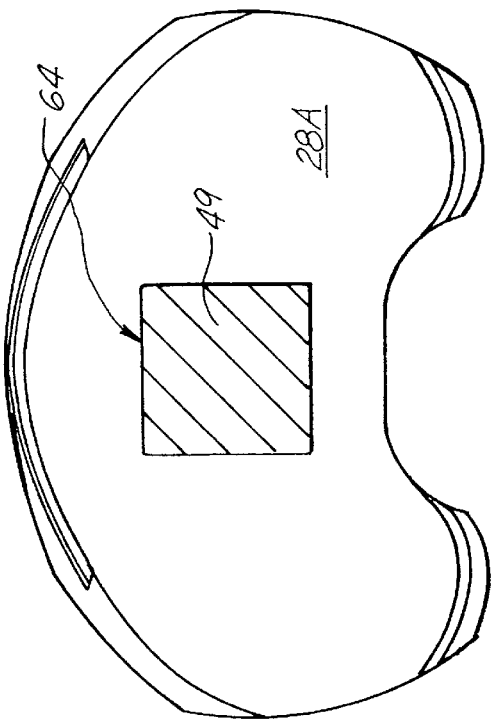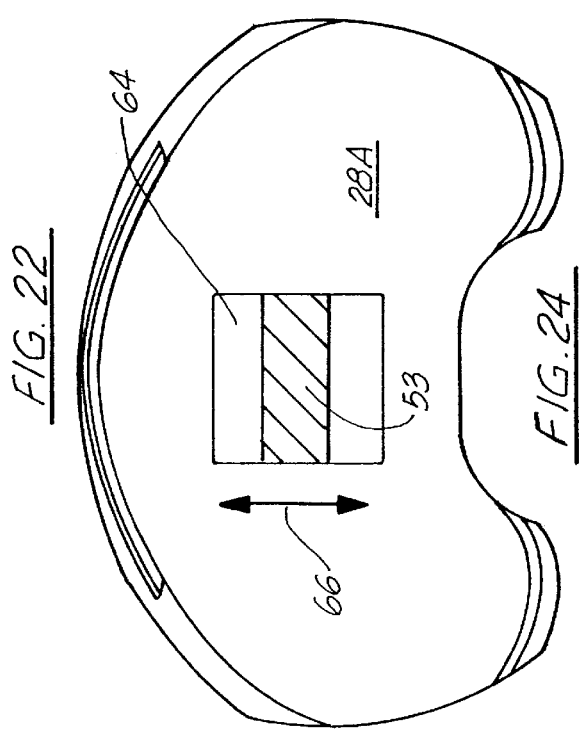

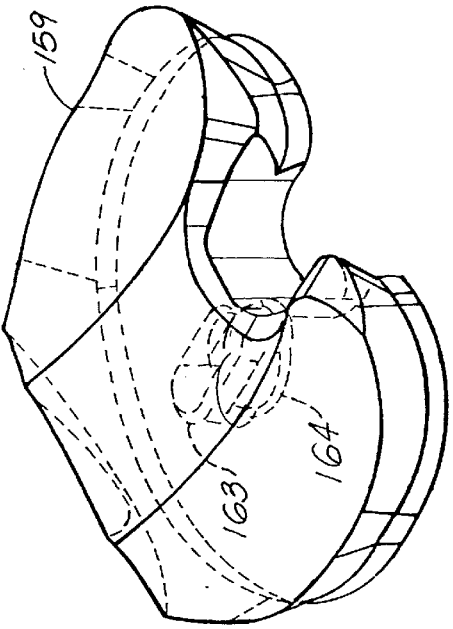
FIG. 40
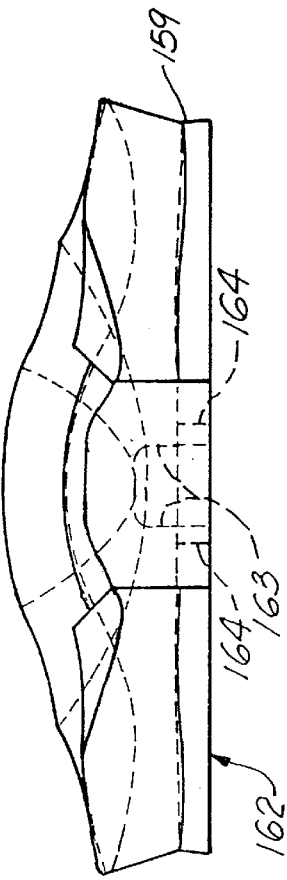
FIG. 42
FIG. 43
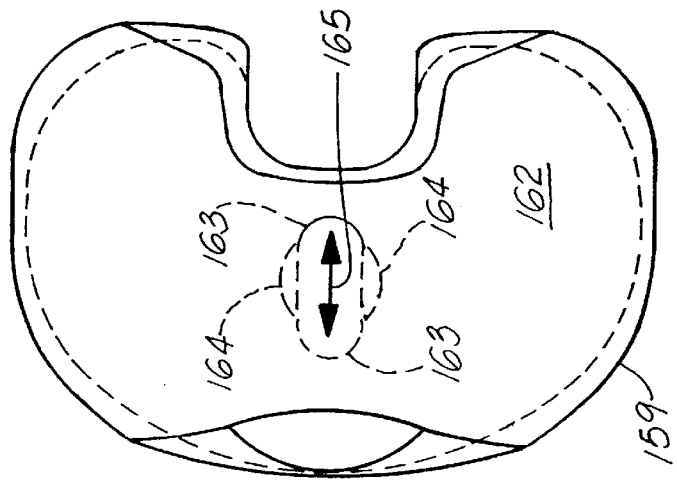
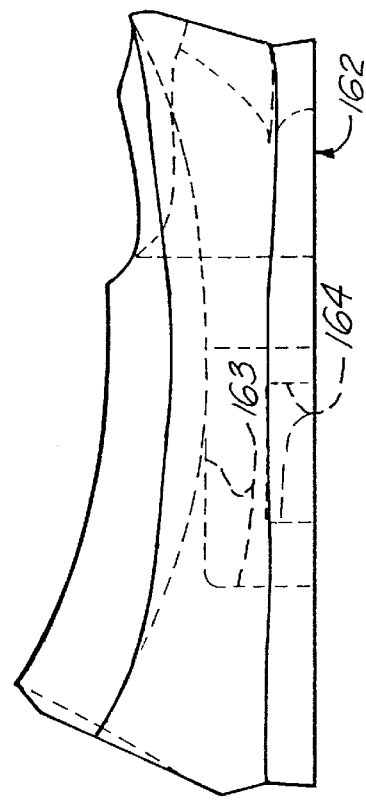
FIG. 41

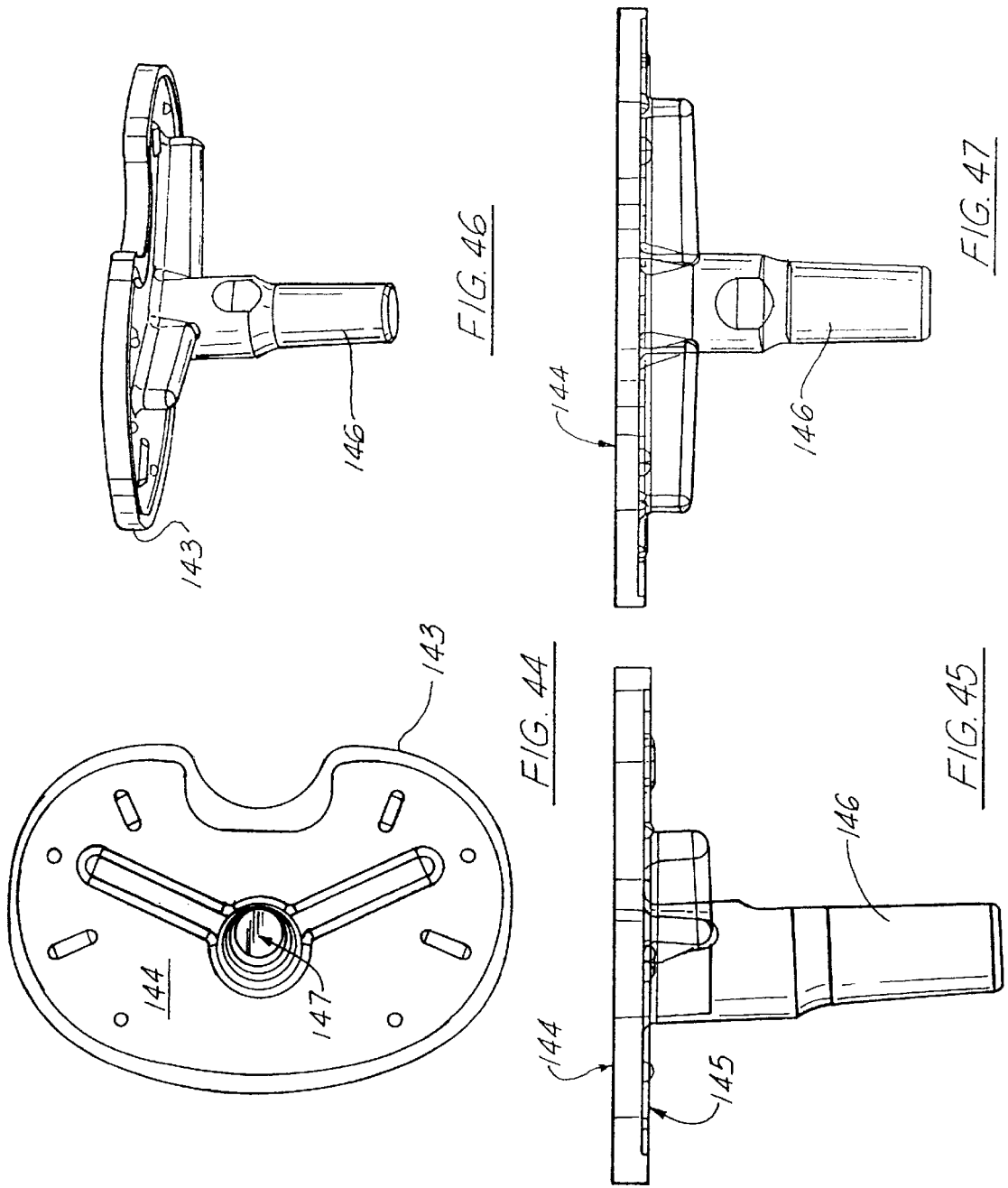

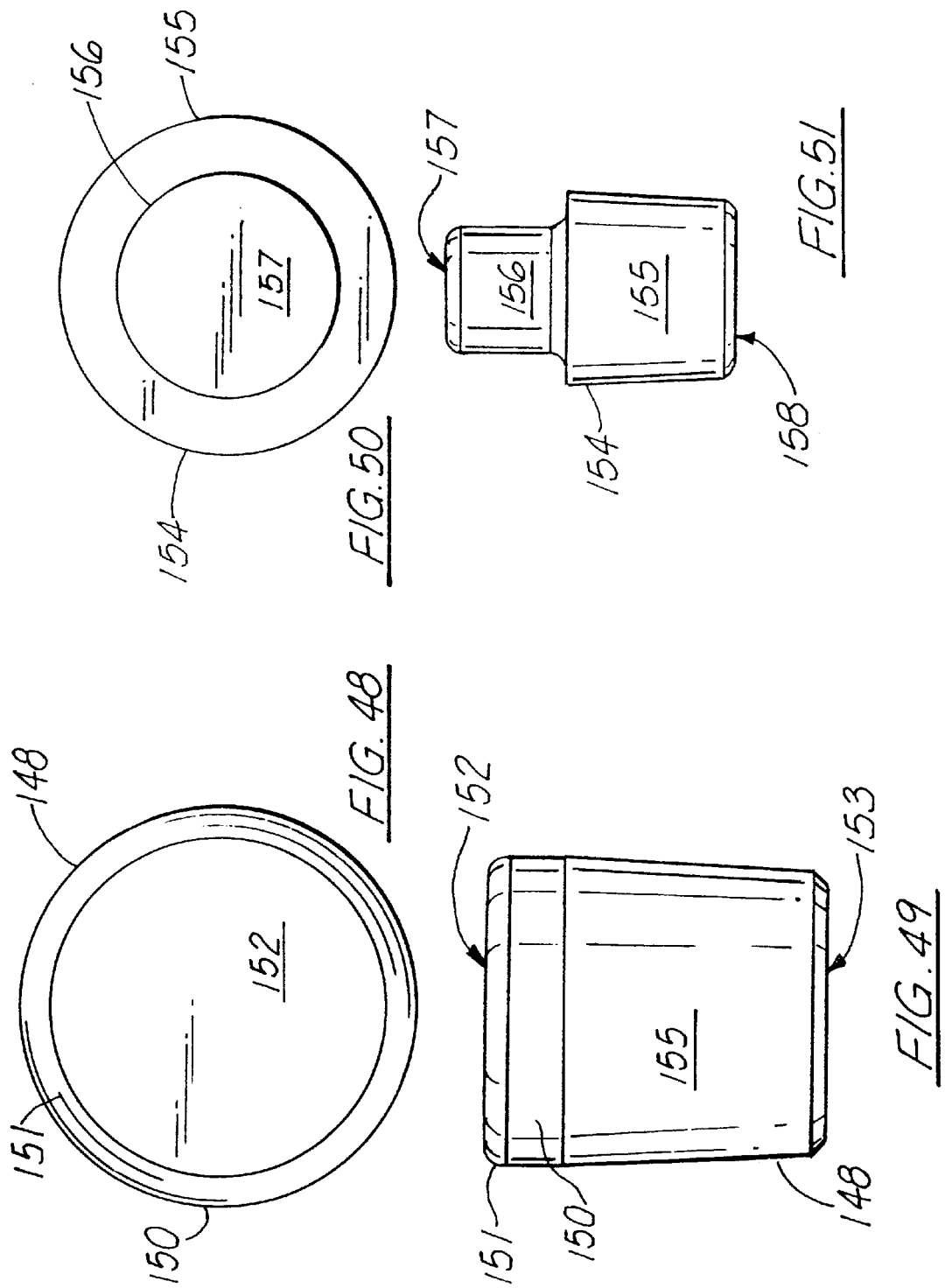

MOBILE BEARING KNEE PROSTHESIS

CROSS-REFERENCE TO RELATED APPLICATIONS

Priority of U.S. Provisional Patent Application Serial No. 60/059,131, filed Sep. 17, 1997, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic prosthetic devices, and more particularly to an improved rotating platform, mobile knee prosthesis that incorporates anterior stabilization along with the ability to constrain the movement of the articular surface from rotation and translation, to rotation only.

2. General Background of the Invention

Previous rotating platform designs have incorporated rotating only or rotation and translation through the use of different prostheses. An example of a prosthesis that rotates and translates is shown in British publication 2219942, entitled "Knee Prosthesis".

The present invention has as an object a tibial base plate and mating articular insert with specially configured stabilization posts. The invention enables for the surgeon to convert a mobile bearing articular surface from a fixed to a rotating only or translating only. The prosthesis can also provide both rotation and translation simultaneously.

These conversions are accomplished with special locking members or plugs that connect to the tibial base special plate. The plugs can be secured to the base plate with a taper lock or a threaded connection for example.

A post on the proximal tibial base plate can be positioned with an offset with respect to an oval hole in the articular insert to provide anterior stabilization in the total knee prosthesis.

The prosthesis of the present invention will be used as part of a total knee surgery when the surgeon chooses to use a prosthesis that incorporates a particular, selected relative motion between tibial tray and tibial insert.

BRIEF DESCRIPTION OF THE SEVERAL VIEW OF THE DRAWINGS

For a further understanding of the nature, objects, and advantages of the present invention, reference should be had to the following detailed description, read in conjunction with the following drawings, wherein like reference numerals denote like elements and wherein:

FIG. 5 is a rear, elevational and exploded view of the preferred embodiment of the apparatus of the present invention illustrating the articular polymeric insert and tray portions thereof;

FIG. 6 is a sectional, elevational view of the preferred embodiment of the apparatus of the present invention shown with the locking member removed;

FIG. 7 is another sectional, elevational view of the preferred embodiment of the apparatus of the present invention illustrating the locking member in operating position when only rotational movement is desired;

FIG. 8 is a partial top view of the preferred embodiment of the apparatus of the present invention showing the polymeric insert;

FIG. 9 is a partial, bottom view of the preferred embodiment of the apparatus of the present invention showing the polymeric insert;

FIG. 10 is a partial rear view of the preferred embodiment of the apparatus of the present invention showing the polymeric insert;

FIG. 11 is a partial sectional view of the preferred embodiment of the apparatus of the present invention taken along lines 11—11 of FIG. 8;

FIG. 12 is a sectional view of the preferred embodiment of the apparatus of the present invention taken along lines 12—12 of FIG. 8;

FIGS. 18–21 are fragmentary perspective views of an alternate embodiment of the apparatus of the present invention illustrating constructions for the post portion and illustrating the connection between the post and the tray;

FIGS. 22–25 are schematic plan views of alternate constructions of the tibial insert to be used respectively with the post constructions of FIGS. 18–21;

FIG. 40 is a partial top view of the third alternate embodiment of the apparatus of the present invention illustrating the insert portion thereof;

FIG. 41 is a side view of the insert portion of the third alternate embodiment of the apparatus of the present invention;

FIG. 42 is a perspective view of the insert portion of the third alternate embodiment of the apparatus of the present invention;

FIG. 43 is a posterior view of the insert portion of the third alternate embodiment of the apparatus of the present invention;

FIG. 44 is a bottom view of the tray portion of the third alternate embodiment of the apparatus of the present invention;

FIG. 45 is a side view of the tray portion of the third alternate embodiment of the apparatus of the present invention;

FIG. 46 is a perspective view of the tray portion of the third alternate embodiment of the apparatus of the present invention;

FIG. 47 is a posterior view of the tray portion of the third alternate embodiment of the apparatus of the present invention;

FIGS. 48–49 are fragmentary views of the third alternate embodiment of the apparatus of the present invention illustrating one of the plug portions thereof; and FIGS. 50–51 are side and top views of a second plug portion that is used with the third alternate embodiment of the apparatus of the present invention.

DETAILED DESCRIPTION OF THE INVENTION

Figure 1:
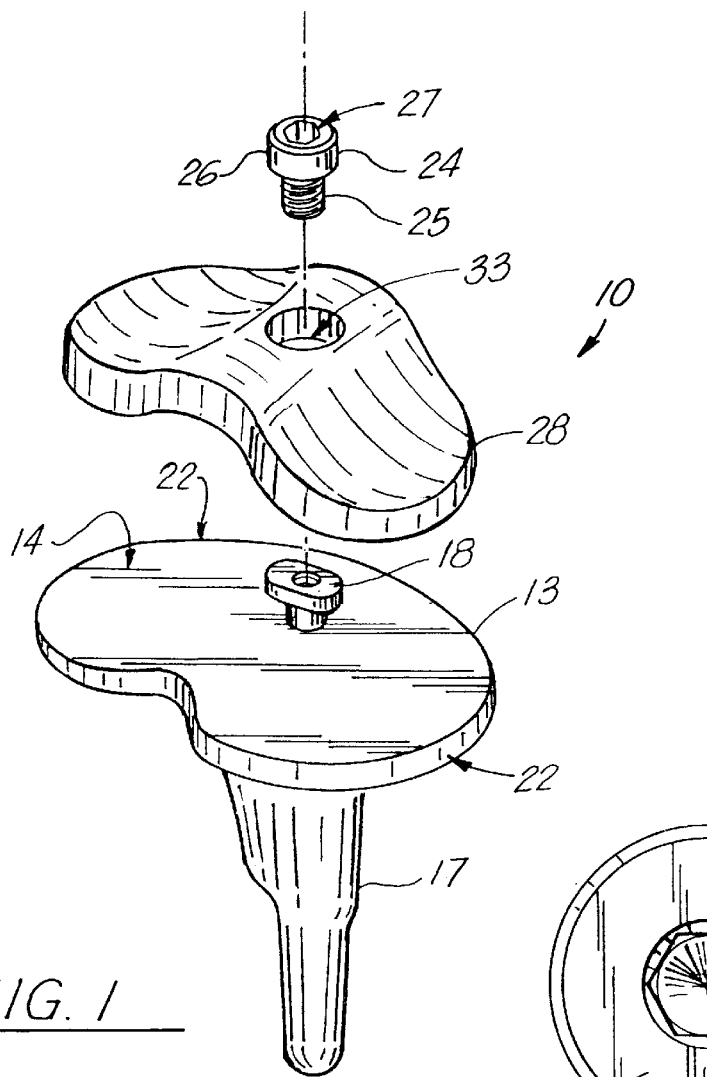
FIG. 1 is a perspective, exploded view of the preferred embodiment of the apparatus of the present invention.
Figure 3:
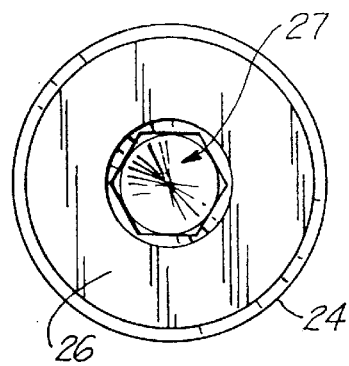
FIG. 3 is a top, fragmentary view of the preferred embodiment of the apparatus of the present invention illustrating the locking member portion thereof.
Figure 2:
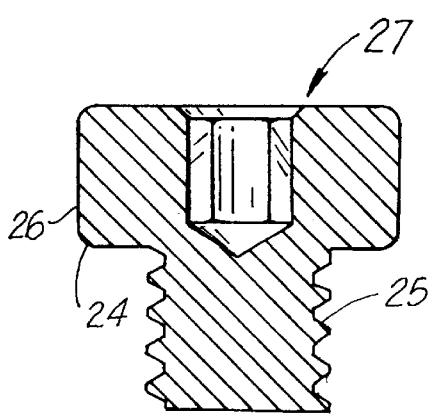
FIG. 2 is a partial sectional of the preferred embodiment of the apparatus of the present invention illustrating the locking member portion thereof.
Figure 4:
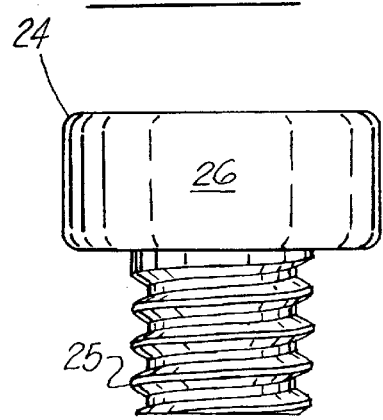
FIG. 4 is a partial, elevational view of the preferred embodiment of the apparatus of the present invention illustrating the locking member portion thereof.

FIGS. 1–7 show generally the preferred embodiment of the apparatus of the present invention designated generally by the numeral 10 in FIGS. 1, 6, and 7.

Mobile bearing knee prosthesis 10 is placed upon a patient's surgically cut proximal tibia 11 at a surgically cut proximal surface 12 that is preferably flat. This enables a tray 13 to be mounted to the proximal tibia 11 at surface 12 as shown in FIGS. 6 and 7. Tray 13 has a flat proximal surface 14 and a generally flat distal surface 15 that mates with and faces the surgically prepared surface 12 as shown in FIGS. 6–7. The tray 13 can provide a plurality of spikes 16 and a stem 17 for enhancing implantation to the patient's proximal tibia 11.

The proximal surface 14 of tray 13 provides a post 18 having an internally threaded socket 19.

Figure 13:
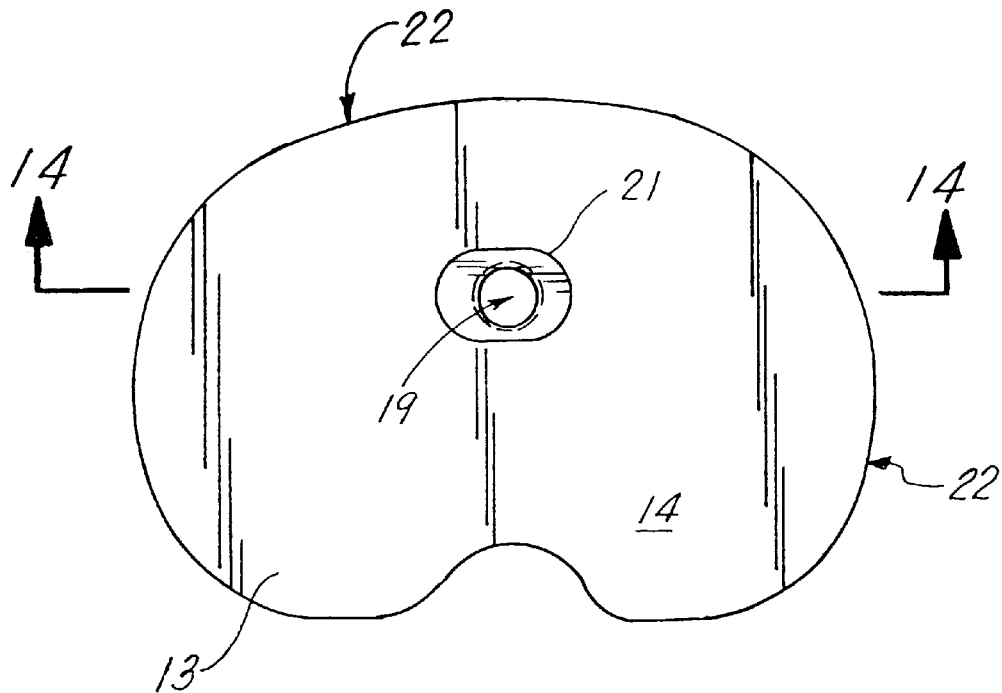
FIG. 13 is a partial top view of the preferred embodiment of the apparatus of the present invention illustrating the tray.
Figure 14:
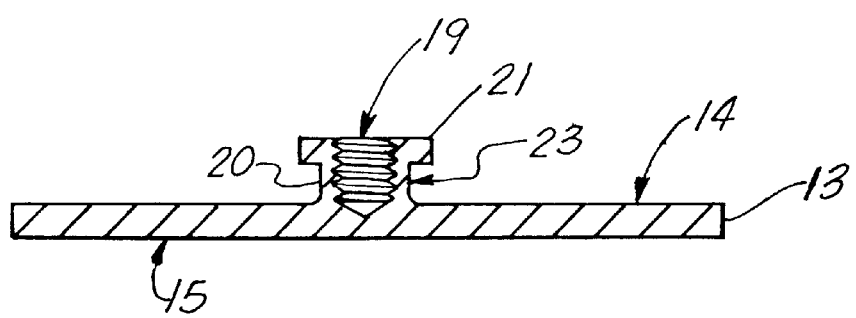
FIG. 14 is a sectional view of the preferred embodiment of the apparatus of the present invention taken along lines 14—14 of FIG. 13.

Post 18 is comprised of a generally cylindrically-shaped smaller diameter section 20 and an enlarged flange 21 that mounts to the top of cylindrically-shaped 20 as shown in FIGS. 5 and 13–14. Tray 13 has a periphery 22. A recess 23 is provided in between the proximal surface 14 of tray 13 and flange 21.

A locking member 24 forms a removable connection with the socket 19. Locking member 24 has an externally cylindrical section 25 that provides threads that correspond to the threads of internally socket 19 so that the locking member 24 can be threaded into the socket 19 as shown in FIG. 7. Locking member 24 includes an enlarged cylindrically-shaped head 26 having a tool receptive socket 27 such as a hexagonal socket for example.

A polymeric insert 28 provides a vertical channel 33 that can be placed in communication with post 18 as shown in FIGS. 6 and 7. Insert 28 provides a preferably flat distal surface 29 that communicates with the flat proximal surface 14 of tray 13. A pair of spaced apart concavities 30, 31 are provided for defining articulation surfaces that cooperate with correspondingly shaped articulating surface on a patient's femur or femoral implant. The insert 28 has a periphery 32 that generally corresponds in shape to the periphery 22 of tray 13.

Vertical channel 33 is comprised of a number of sections that are specially shaped to interact with the post 18 and locking member 24. Vertical channel 33 thus includes a proximal, cylindrically-shaped section 34, an oval shaped slot 35, and a distal opening 36. The distal opening 36 includes a generally oval section 37 and a somewhat half oval section 38. Flat surfaces 39, 40 are positioned at the top of and at the bottom of the oval shaped slot 35 as best seen in FIGS. 8–11. The cylindrically-shaped head 26 of locking member 24 closely fits the cylindrically-shaped section 36.

In order to assemble insert 28 to tray 13, the distal surface of 29 of insert 28 is placed next to and generally parallel to the proximal surface 14 of tray 13. Post 18 is aligned with vertical channel 33 of insert 28. During assembly of insert 28 to tray 13, the post 18 is shaped to enter the oval opening portion 37 of distal opening 36. Once the distal surface 29 of insert 28 meets proximal surface 14 of tray 13, flange 21 aligns with oval shaped slot 35 of vertical channel 33. After such assembly, insert 28 is held in position by post 18. This retention of insert 28 by post 18 occurs when flange 21 engages flat surface 40 to prevent separation if any rotation (see arrow 41 of FIG. 17) at all occurs between insert 28 and tray 13. If no rotation has occurred between insert 28 and tray 13 (see FIG. 15), the oval shaped circular section 37 is sized to allow post 18 to be inserted into or withdrawn from channel 33.

Figure 15:
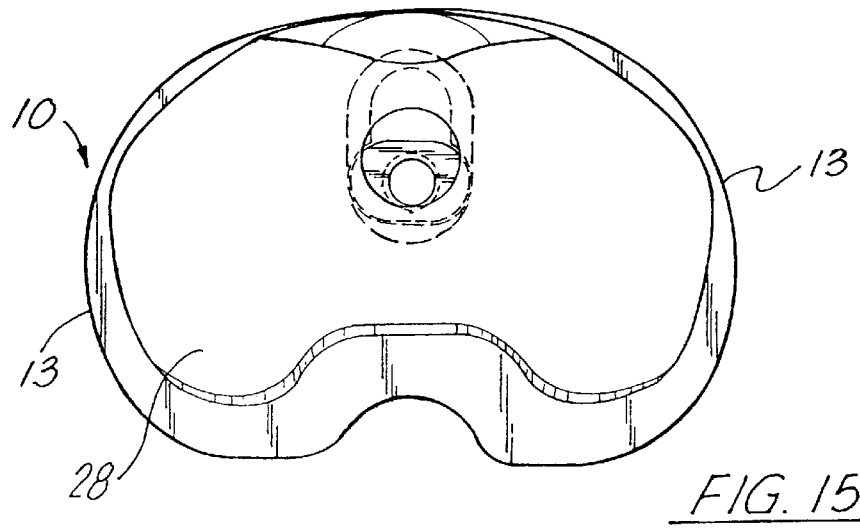
FIG. 15 is a top view of the preferred embodiment of the apparatus of the present invention illustrating the insert and tray portions thereof in operating position without the locking member.
Figure 16:
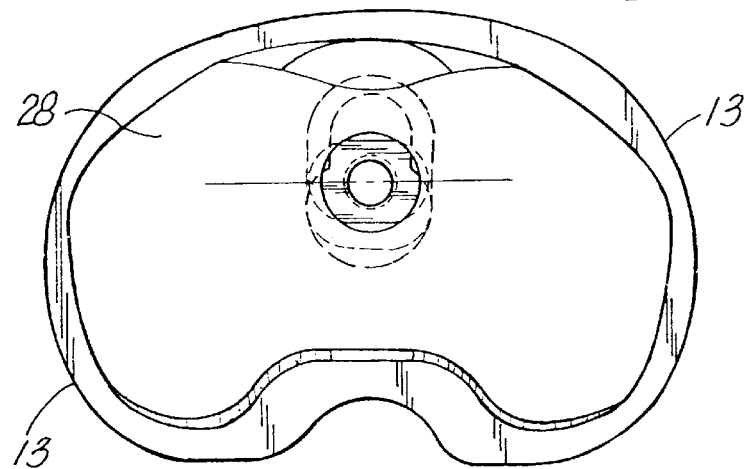
FIG. 16 is a top side view of the preferred embodiment of the apparatus of the present invention illustrating the insert, tray and locking member portions thereof in operating position.
Figure 17:
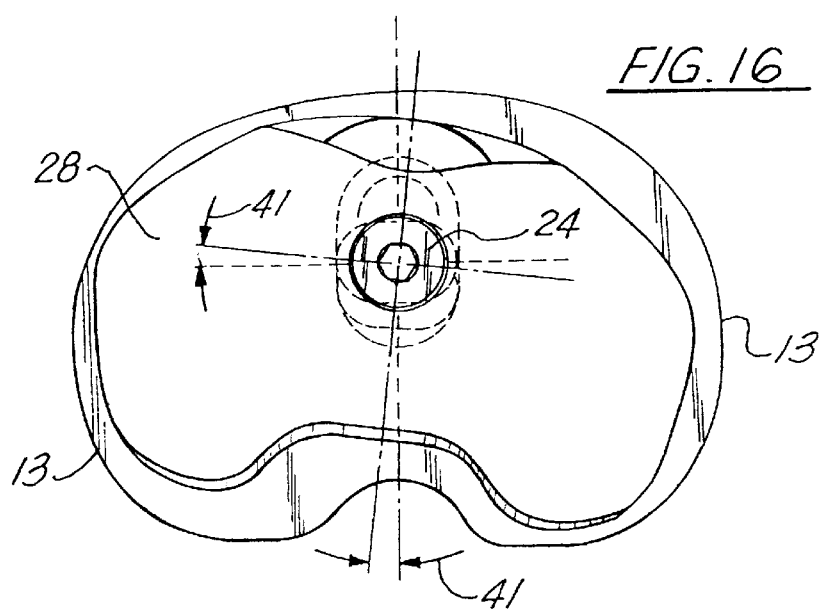
FIG. 17 is a top view of the preferred embodiment of the apparatus of the present invention illustrating rotation of the insert relative to the tray.

In FIG. 15, the apparatus 10 is shown in an assembled position wherein the fastener 24 has been removed so that the insert 28 can move in a translation and rotation and rotation fashion relative to tray 13. In FIG. 16, the fastener 24 has been threadably attached to the internally threaded socket 19 and is in operating position. In FIG. 17, the insert 28 can rotate relative to the tray 13 through an angle 41. However, because of the attachment of fastener 24, only rotation and not translation is permitted in FIG. 17. Thus, in FIG. 17, the apparatus 10 of the present invention provides a mating mechanism between the post 18 and the fastener 24 and the insert 28 that defines a constraining mechanism so that the insert 28 may be constrained for rotation only relative to the tray 13.

In FIGS. 18–21 and 22–25, there is seen various alternate constructions of the post that can be used instead of post 18 when the selected post is fitted to the tibial tray 13. In FIGS. 22–25, an alternate construction of the insert 28 is shown with an illustration of the various types of relative motion between the insert and the tibial tray that can be selectively provided to a surgeon.

In FIGS. 18–21, four different constructions of the post are provided. In FIG. 18, a post 42 has a cylindrical outer surface 43 and a circular top 44. Post 42 has a rectangular base 45 with a generally flat undersurface and a plurality of four inclined surfaces 46 which provides a means of attaching the post to the tray or the post may be permanently attached to the tray. The rectangular base 45 fits tray 13A socket 47 at its inclined surfaces 48 with a taper lock type connection for example. Other types of connections could be used to join post 42 to tray 13A at socket 47.

In FIG. 19, post 49 includes a plurality of four vertical side walls 50 and a plurality of four inclined surfaces 51. A rectangular flat top 52 is provided opposite a generally flat undersurface of post 49. The inclined surfaces 51 of post 49 fit similarly configured inclined surfaces 48 of socket 47 in tray 13A.

In FIG. 20, post 53 is generally rectangularly shaped providing a pair of opposed flat larger vertical side walls 54 and a pair of opposed flat smaller end walls 55 with a flat top 56. Post 53 has a base 57 that includes four inclined surfaces 58. The inclined surfaces 58 form a taper lock connection with four similarly configured inclined surfaces 48 of socket 47 of tray 13A.

In FIG. 21, post 59 has a hexagonal shape providing a hexagonally shaped flat top 60. Hexagonal post 59 also has a plurality of vertical side walls 61 and a rectangular base 62. The base 62 has inclined surfaces 63 that form a taper lock connection with inclined surfaces 48 of tray socket 47 of tray 13A.

In FIG. 22, insert 28A provides a square opening 64 that exactly fits peg 49. In FIG. 22, there is no relative motion between insert 28A and tray 13A. In FIG. 23, rotational motion only is indicated by arrow 65 between insert 28A and tray 13A when peg 42 is used.

In FIG. 24, the rectangular peg 53 enables only translational movement between the insert 28A and tray 13A as indicated by arrow 66. In FIG. 25, the hexagonal peg 59 enables both rotational motion as indicated by arrow 65 and translational motion as indicated by arrow 66 between insert 28A and tray 13A.

Figure 37:
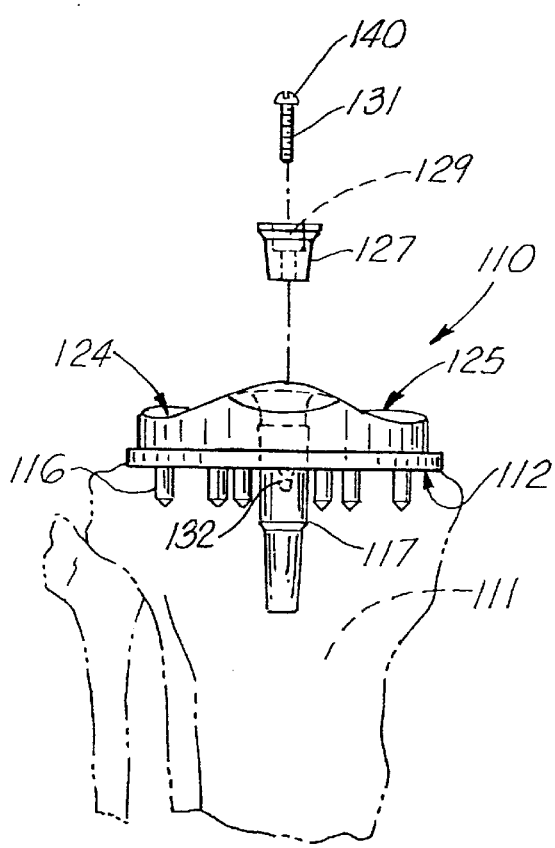
FIG. 37 is an elevational view of the second alternate embodiment of the apparatus of the present invention illustrating the cap and set screw separated from the insert and tray portions thereof.

An alternate embodiment of mobile bearing knee apparatus 110 is shown generally in FIG. 37. In FIG. 37, the prosthesis 110 is shown positioned upon a patient's proximal tibia 111, specifically upon a flat surgically cut proximal surface 112 as shown.

Figure 26:
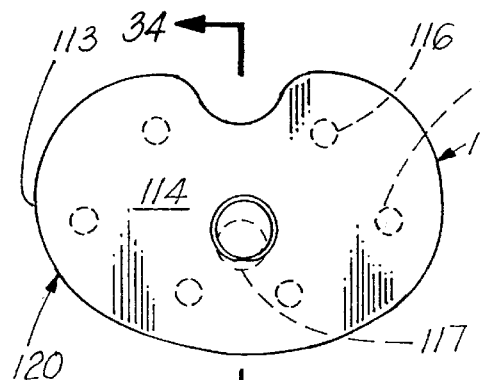
FIG. 26 is a top view of the second alternate embodiment of the apparatus of the present invention illustrating the tray portion thereof.
Figure 27:
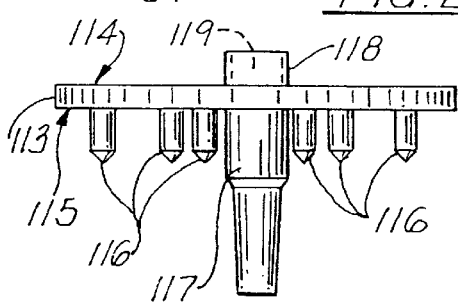
FIG. 27 is an elevational view of the second alternate embodiment of the apparatus of the present invention illustrating the tray portion thereof.
Figure 28:
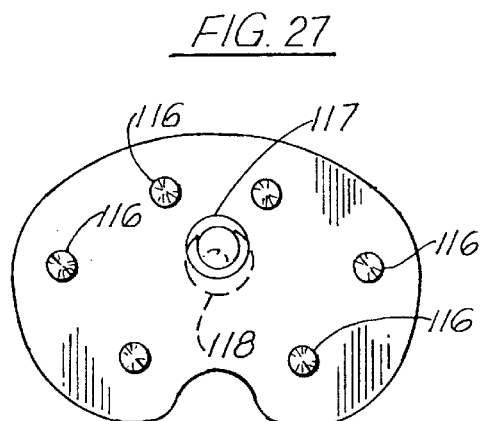
FIG. 28 is a bottom view of the second alternate embodiment of the apparatus of the present invention illustrating the tray portion thereof.

In FIGS. 26–28, tibial tray 113 is shown, which can be of metallic construction such as titanium alloy, for example. Tray 113 has a flat proximal surface 114 and a flat distal surface 115. A plurality of spikes 116 on surface 115 can be used to enhance fixation of tibial tray 113 to the patient's proximal tibial 111. A stem 117 can also be used to facilitate attachment of prosthesis 110 to the patient's tibia 111 at the tibial intramedullary canal.

The flat proximal surface 114 of tray 113 has a round post 118 with a hollow bore or socket 119. The post 118 is spaced inwardly from the periphery 120 of tray 113 as shown in FIGS. 26 and 27. The post 118 is preferably positioned with an offset with respect to oval slot 126 in the articular insert to provide anterior stabilization in the total knee prosthesis.

Figure 29:
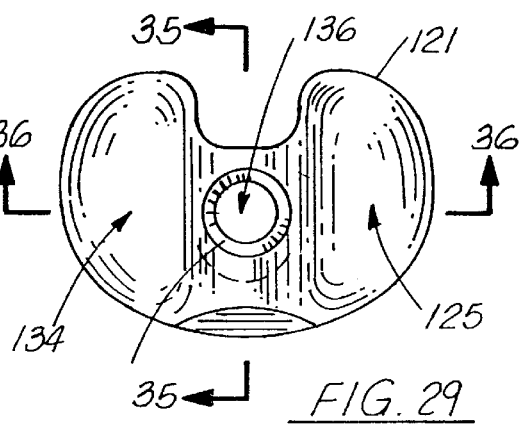
FIG. 29 is a plan view of the second embodiment of the apparatus of the present invention illustrating the polymeric insert portion thereof.
Figure 30:
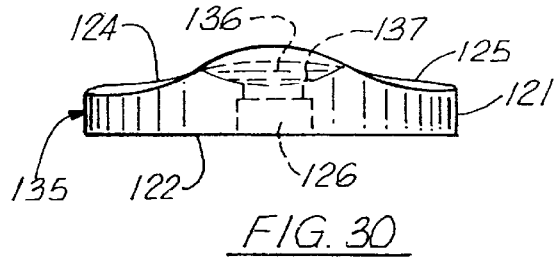
FIG. 30 is a frontal elevational view of the second alternate embodiment of the apparatus of the present invention illustrating the plastic insert portion thereof.
Figure 31:
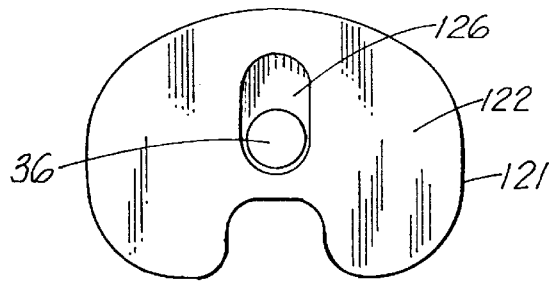
FIG. 31 is a bottom view of the plastic insert portion of the second alternate embodiment of the apparatus of the present invention.

FIGS. 29–31 show the insert 121 portion of the present invention, typically a polymeric plastic insert that fits tray 113. Insert 121 has a flat distal surface 122 and a proximal surface 123 that includes curved portions. These curved portions are in the form of concavities 124, 125 receive shaped surfaces of a femoral prosthesis after total knee joint replacement surgery is completed. The flat distal surface 122 of insert 121 has an anterior to posterior extending generally oval shaped slot 126 as shown in FIG. 31.

The slot 126 receives post 118 during use, enabling the insert 121 to slide in an anterior to posterior direction relative to tray 113.

The present invention provides a rotating platform, mobile knee prosthesis 110 that incorporates anterior stabilization along with the ability to selectively constrain the movement of the articular surface from rotation and translation to rotation only. This is accomplished by using an opening 136 in insert 121 that communicates with slot 126 as shown in FIGS. 29–31 and 35–38. The opening includes a frustoconical portion 137 that corresponds in shape to a similar frustoconically-shaped enlarged annular surface 134 of locking plug member 127. The locking plug member 127 is shown more particularly in FIGS. 32, 33, and 37.

Figure 32:
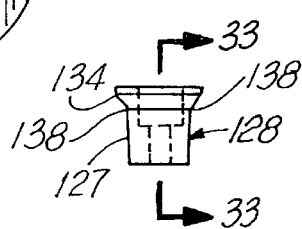
FIG. 32 is a fragmentary view of the second alternate embodiment illustrating the locking plug member portion thereof.
Figure 36:
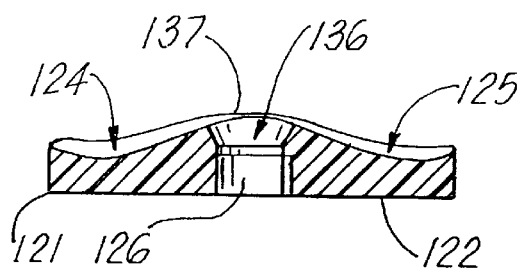
FIG. 36 is a sectional view taken along lines 36—36 of FIG. 29.

Locking plug member 127 includes a lower frustoconical surface 128. The frustoconical outer surface 128 of locking member 127 below annular reference line 138 is sized and shaped to fit and form a taper lock connection with surface 139 of frustoconical socket 119 of post 118. Above annular reference line 138, the enlarged annular shoulder has a frustoconical shape as shown in FIG. 32 that corresponds generally to the size and shape of frustoconical portion 137 of opening 136 as shown in FIG. 36.

When the locking member 127 is first placed through opening 136 of insert 121 and then into frustoconical socket 119 of post 118, a locking connection is formed between the frustoconical outer surface 128 of locking member 127 and the frustoconical surface 139 of post 118. This connection can be a taper lock type connection.

Figure 33:
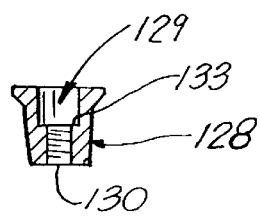
FIG. 33 is a sectional view taken along lines 33—33 of FIG. 32.
Figure 34:
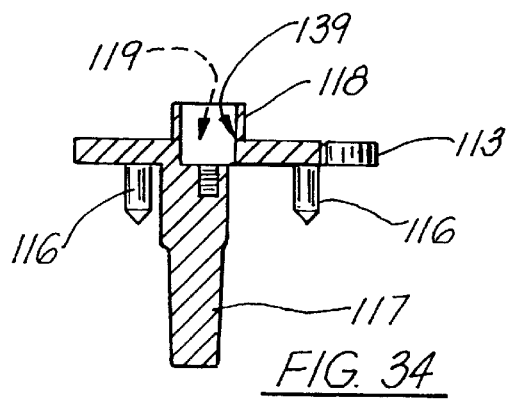
FIG. 34 is a sectional view taken along lines 34—34 of FIG. 26
Figure 35:
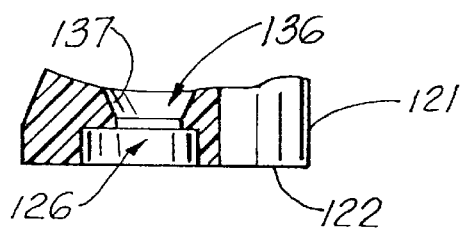
FIG. 35 is a sectional view taken along lines 35—35 of FIG. 29.

Locking screw 131 can be used to engage a correspondingly sized and shaped internally threaded opening 132 of tray 113 if desired. The locking screw 131 can include a head 140 that is enlarged so that the head 140 is retained by annular shoulder 133 of locking member 137 as shown in FIGS. 33 and 37.

Figure 38:
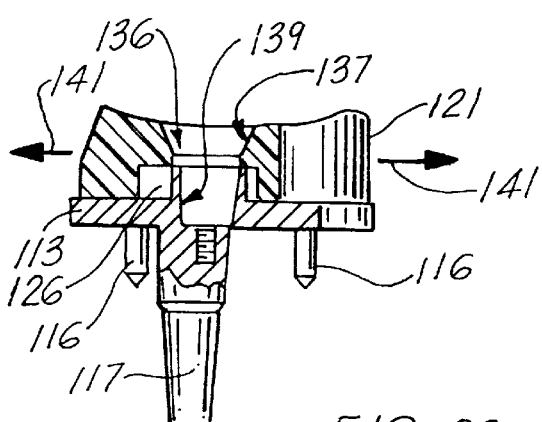
FIG. 38 is a partial sectional elevational view of the second alternate embodiment of the apparatus of the present invention illustrating the mobile insert moving with respect to the tray.

In FIG. 38, arrows 141 indicate sliding movement of insert 121 relative to tray 113 as occurs when locking plug member 127 is removed. In such a situation, the insert 121 is free to slide with respect to tray 113. The distal surface 122 of insert 121 slides upon the flat proximal surface 114 of tray 113. Post 118 slides relative to slot 126.

When locking member 127 is inserted through opening 136 and into socket 119 of post 118, sliding movement is prevented. The enlarged annular shoulder 134 of locking member 127 engages the frustoconical portion 137 of opening 136 disallowing a sliding action of insert 121 relative to tray 113. However, the enlarged annular shoulder 134 of locking member 127 is slightly spaced from frustoconical portion 137 of opening 136, so that rotational movement of insert 121 relative to tray 113 is permitted. The second alternate embodiment of the present invention provides a rotating platform, mobile knee prosthesis 110 that incorporates anterior stabilization along with the ability to constrain movement of the articular surface from rotation and translation to rotation only.

Figure 39:
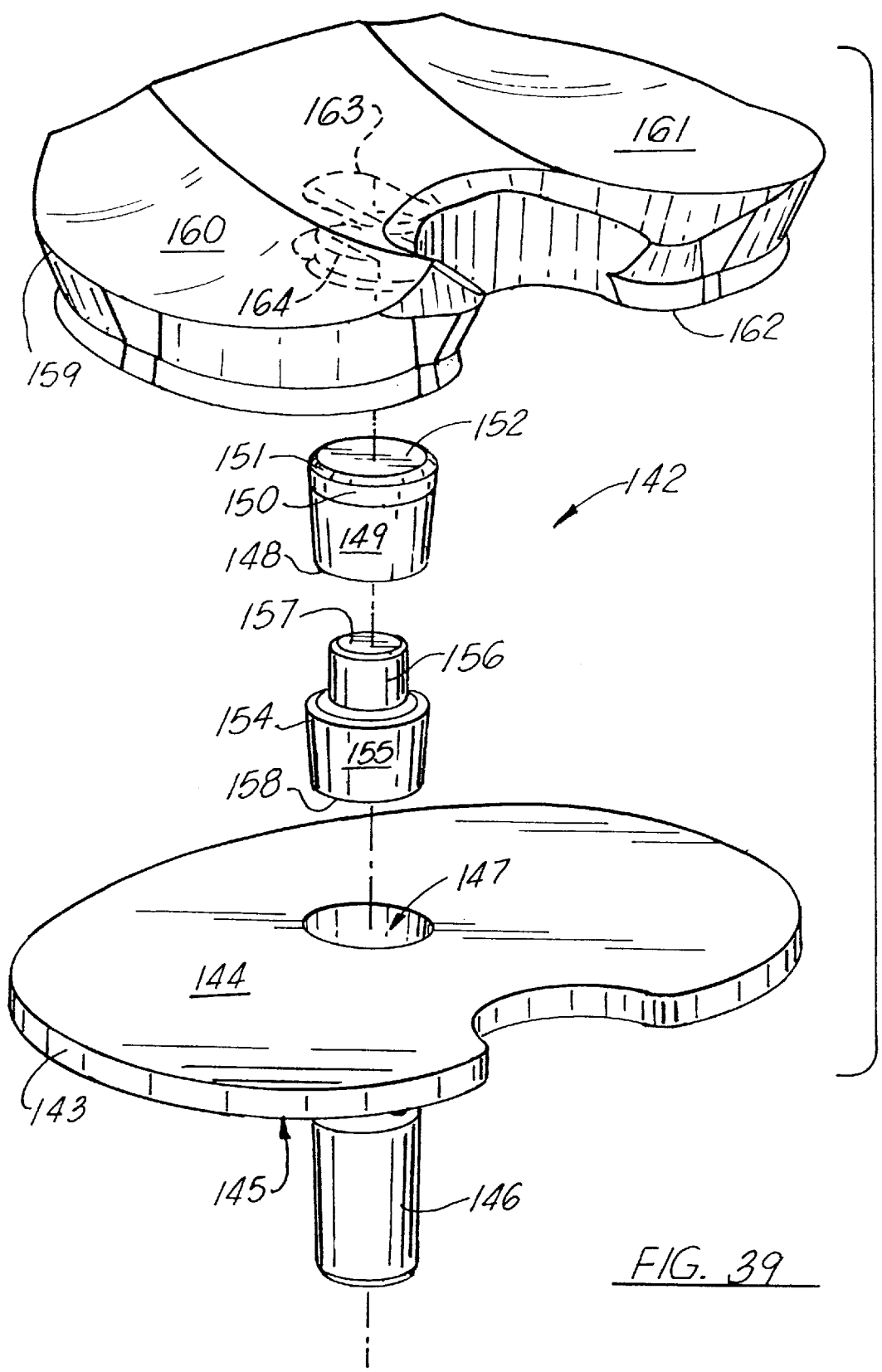
FIG. 39 is a perspective exploded view of a third alternate embodiment of the apparatus of the present invention.

FIGS. 39 and 40–51 show a third alternate embodiment of the apparatus of the present invention designated generally by the numeral 142 in FIG. 39. Mobile bearing knee prosthesis 142 includes a tray 143 that can be attached to a patient's surgically cut proximal tibia using a stem 146 for example that occupies the patient's intramedullary canal. The tray 143 has a proximal surface 144 that receives an insert 159 and a distal surface 145 that registers upon the proximal tibia after the tibia has been surgically prepared to conform to the underside or distal surface 145 of tray 143.

The proximal 144 surface of tray 143 provides a frustoconically-shaped socket 147 that can receive either of two selected plugs 148 or 154 (or any of the plug embodiments shown in FIGS. 18–21). The first plug 148 is designed to provide rotational movement only between insert 159 and tray 143. The plug 148 has a frustoconical surface 149, cylindrical surface 150, beveled annular surface 151, and a pair of opposed generally parallel flat end surfaces 152, 153.

The second plug 154 is designed to provide both anterior to posterior translational movement between the insert 159 and tray 153 as well as rotational movement between the insert 159 and tray 153. The plug 154 has a frustoconical surface 155, a reduced diameter cylindrical surface 156, and flat end surfaces 157, 158.

During use, a surgeon selects either of the plugs 148 or 154. The frustoconical surfaces 149 or 155 form a tight taper lock fit with a correspondingly shaped frustoconical socket 147 that communicates with the proximal 144 surface of tray 143. Once the selected plug 148 or 154 has been inserted into frustoconical socket 147, the insert 159 is placed on the selected plug 148 or 154. The shape of the plug 148 or 154 that is selected determines whether or not the insert 159 can achieve only rotational movement relative to tray 143 or both rotational and anterior to posterior translational movement.

In the case of the plug 148, only rotational movement between the insert 159 and the tray 143 can be attained. The plug 148 is shorter and thus only communicates with the cylindrically-shaped opening 164 on the bottom or distal surface 162 of insert 159. Plug 148 once inserted in socket 147 only enables a rotational movement of the insert 159 on the tray 143. The cylindrical surface 150 of plug 148 corresponds in size and shape to the circular opening 164 to accomplish a relatively close fit between cylindrical surface 150 of plug 148 and cylindrical opening 164 on insert 159.

When both rotational and translational anterior to posterior movement are desired, the surgeon selects the plug 154. The plug 154 is placed in socket 147 so that frustoconical surface 155 forms a taper lock fit with a correspondingly sized and shaped socket 147 of tray 143. The smaller cylindrically-shaped portion 156 of plug 154 is taller in a proximal to distal direction than the cylindrically-shaped portion 150 of plug 148. The portion 156 fits elongated slot 163 so that the insert 159 can translate in an anterior to posterior direction as the reduced diameter cylindrical portion 156 travels anterior to posterior in the direction of arrow 165 in FIG. 44. Because the slot 163 is at least as wide as the diameter of cylindrical portion 156, rotational movement is also available between insert 159 and tray 143. Insert 159 also provides proximal concavities 160, 161 for recieving a femoral component of a knee implant.

PARTS LIST

The following is a list of suitable parts and materials for the various elements of the preferred embodiment of the present invention.

| Part Number | Description |
| --- | --- |
| 10 | mobile bearing knee prosthesis |
| 11 | tibia |
| 12 | surgically cut proximal surface |
| 13 | tray |
| 13A | tray |
| 14 | flat proximal surface |
| 15 | flat distal surface |
| 16 | spike |
| 17 | stem |
| 18 | post |
| 19 | internally threaded socket |
| 20 | cylindrically-shaped section |
| 21 | flange |
| 22 | periphery |
| 23 | recess |
| 24 | fastener |
| 25 | externally threaded section |
| 26 | head |
| 27 | tool receptive socket |
| 28 | insert |
| 29 | flat distal surface |
| 30 | concavity |
| 31 | concavity |
| 32 | periphery |
| 33 | vertical channel |
| 34 | proximal, cylindrically-shaped section |
| 35 | oval shaped slot |
| 36 | distal opening |
| 37 | oval section |
| 38 | half oval section |
| 39 | flat surface |
| 40 | flat surface |
| 41 | arrow/angle |
| 42 | post |
| 43 | cylindrical surface |
| 44 | circular top |
| 45 | rectangular base |
| 46 | inclined side wall |
| 47 | tray socket |
| 48 | inclined surface |
| 49 | post |
| 50 | vertical side wall |
| 51 | inclined surface |
| 52 | flat top |
| 53 | post |
| 54 | vertical side wall |
| 55 | vertical end wall |
| 56 | flat top |
| 57 | rectangular base |
| 58 | inclined surface |
| 59 | post |
| 60 | flat top |
| 61 | vertical side wall |
| 62 | rectangular base |
| 63 | inclined surface |
| 64 | insert opening |
| 65 | arrow |
| 66 | arrow |
| 110 | mobile bearing knee prosthesis |
| 111 | tibia |
| 112 | surgically cut proximal surface |
| 113 | tray |
| 114 | flat proximal surface |
| 114A | opening |
| 115 | flat distal surface |

-continued

| Part Number | Description |
| --- | --- |
| 116 | spike |
| 117 | stem |
| 118 | post |
| 119 | socket |
| 120 | periphery of tray |
| 121 | insert |
| 122 | flat distal surface |
| 123 | proximal surface |
| 124 | concavity |
| 125 | concavity |
| 126 | slot |
| 127 | locking plug member |
| 128 | frustoconical outer surface |
| 129 | socket |
| 130 | threaded bore |
| 131 | locking screw |
| 132 | internally threaded opening |
| 133 | annular shoulder |
| 134 | enlarged annular shoulder |
| 135 | periphery of insert |
| 136 | opening |
| 137 | frustoconical portion |
| 138 | annular reference line |
| 139 | frustoconical surface |
| 140 | enlarged head |
| 141 | arrows |
| 142 | mobile bearing knee prosthesis |
| 143 | tray |
| 144 | proximal surface |
| 145 | distal surface |
| 146 | stem |
| 147 | frustoconical socket |
| 148 | plug |
| 149 | frustoconical surface |
| 150 | cylindrical surface |
| 151 | beveled annular surface |
| 152 | flat end surface |
| 153 | flat end surface |
| 154 | plug |
| 155 | frustoconical surface |
| 156 | reduced diameter cylindrical surface |
| 157 | flat end surface |
| 158 | flat end surface |
| 159 | insert |
| 160 | proximal concavity |
| 161 | proximal concavity |
| 162 | flat distal surface |
| 163 | elongated slot |
| 164 | cylindrical opening |
| 165 | arrow |

The foregoing embodiments are presented by way of example only; the scope of the present invention is to be limited only by the following claims.

What is claimed is:

1. A knee prosthesis apparatus comprising:
   a) a tibial tray portion adapted to be surgically implanted on a patient's transversely cut proximal tibia;
   b) a femoral component;
   c) a fixator for holding the tray on the patient's proximal tibia;
   d) a tibial insert having a proximal surface that is shaped to engage a femoral component, the insert having a distal surface that fits against and articulates with the proximal surface of the tibial tray;
   e) a constraining mechanism that joins the tibial insert to the tibial tray portion during use in a selective fashion that enables a number of different possible relative motions between the tibial insert and tibial tray portion including anterior to posterior translation and rotation, rotation only, translation only, or no relative motion;
   f) wherein all or part of the constraining mechanism is separable from the tray and selective removal of all or part of the constraining mechanism determines which of the said possible relative motions will take place.

2. The knee prosthesis of claim 1 wherein the proximal surface of the insert has one or more concavities for articulating with the femoral component.

3. The knee prosthesis of claim 1 wherein there are two concavities that define the proximal surface.

4. The knee prosthesis of claim 1 wherein the constraining mechanism includes a post extending up from the proximal surface of the tibial tray.

5. The knee prosthesis of claim 4 wherein the constraining mechanism includes a locking plug member that fits a socket on the post.

6. The knee prosthesis of claim 1 wherein the removable constraining mechanism includes a post extending up from the proximal surface of the tibial tray, a slot on the distal surface of the insert, an opening on the proximal surface of the insert that communicates with the slot and a locking plug member that can access the post from the proximal surface of the insert via the opening.

7. The knee prosthesis of claim 6 wherein the removable constraining mechanism includes a socket on the post that receives the locking plug member when the locking plug member is attached to the post for further defining movement between the insert and the tray.

8. The knee prosthesis of claim 6 wherein the opening is defined by an annular surface that fits closely to the locking plug member when the locking plug member is connected to the post.

9. A knee prosthesis apparatus comprising:
   a) a tibial tray portion adapted to be surgically implanted on a patient's transversely cut proximal tibia;
   b) a fixator for holding the trap on the patient's proximal tibia;
   c) a tibial insert having a proximal surface that engages the femoral component, the insert having a distal surface that fits against and articulates with the proximal surface of the tray;
   d) a constraining mechanism that joins the insert to the tray during use in a selective fashion that enables a number of different possible relative motions between the insert and tibial tray including anterior to posterior translation and rotation, rotation only, translation only, or no relative motion;
   e) wherein all or part of the mating mechanism is separable from the tray and selective removal of all or part of the constraining mechanism determines which of the said possible relative motions will take place, wherein the constraining mechanism includes an opening that extends from the proximal to the distal surface of the insert and a variety of connectable portions which are selectively attachable to or separable from the tray, and wherein the geometry of the various connectable portions relative to the opening enables a user to determine which of the relative motions will take place.

10. A knee prosthesis comprising:
    a) a tibial component having a tibial tray adapted to be surgically implanted on a patient's surgically cut proximal tibia;
    b) a fixator for holding the tibial tray on the patient's proximal tibia;
    c) a tibial insert having a distal surface that fits against and articulates with the proximal surface of the tray, the insert having condylar surfaces that engage but do not substantially constrain condylar surfaces of the femoral component;

d) a constraining mechanism that can selectively join the tibial insert to the tray during use to define any of a number of relative motions between the tray and the tibial insert, including rotation only, anterior to posterior translation only, anterior to posterior translation and rotation, or no relative motion;

e) wherein said constraining mechanism includes a post extending up from the tray, a slot in the insert that fits about the post, the slot enabling both anterior to posterior translation of the insert relative to the tray; and f) wherein the constraining mechanism further includes a removable locking plug member that can collect to or disconnect from the post, wherein the insert is further constrained relative to the tray when the removable locking plug member is connected to the post.

11. The knee prosthesis of claim 10 wherein the slot extends through the insert, communicating with both the proximal and distal surfaces of the insert.

12. The knee prosthesis of claim 10 wherein the slot has a generally cylindrically-shaped section that communicates with the proximal surface of the insert.

13. A knee prosthesis comprising:

a) a tibial component having a tray portion adapted to be surgically implanted on a patient's surgically cut proximal tibia;

b) a fixator for holding the tray on the patient's proximal tibia;

c) a tibial insert having a distal surface that fits against and articulates with the proximal surface of the tray;

d) a constraining mechanism that can selectively join the insert to the tray during use to define any of a number of relative motions between tray and the tibial insert and including rotation only, anterior to posterior translation only, anterior to posterior translation and rotation, or no relative motion;

e) wherein said constraining mechanism includes a post extending up from the tray, a slot in the insert that fits about the post, the slot enabling both anterior to posterior translation of the insert relative to the tray; and f) wherein the constraining mechanism further includes a removable locking plug member that can connect to or disconnect from the post, wherein the insert is further constrained relative to the tray when the removable locking plug member is connected to the post, wherein the slot has an elongated section that communicates with the distal surface of the insert.

14. A knee prosthesis comprising:

a) a tibial component having a tray portion adapted to be surgically implanted on a patient's surgically cut proximal tibia;

b) a fixator for holding the tray on the patient's proximal tibia;

c) a tibial insert having a distal surface that fits against and articulates with the proximal surface of the tray;

d) a constraining mechanism that can selectively join the insert to the tray during use to define any of a number of relative motions between the tray and the tibial insert and including rotation only, anterior to posterior translation only, anterior to posterior translation and rotation, or no relative motion;

e) wherein said constraining mechanism includes a post extending up from the tray, a slot in the insert that fits about the post, the slot enabling both anterior to posterior translation of the insert relative to the tray; and f) wherein the constraining mechanism further includes a removable locking plug member that can connect to or disconnect from the post, wherein the insert is further constrained relative to the tray when the removable locking plug member is connected to the post, wherein the slot has a larger transverse cross section at the distal surface of the insert and a smaller transverse cross section at the proximal surface of the insert.

15. A knee prosthesis apparatus comprising:

a) a tibial component that includes a tibial tray adapted to be surgically implanted on a patient's surgically cut proximal tibia;

b) a post mounted at the central portion of the proximal surface of the tray, the post having a socket;

c) a tibial insert having an articulation surface for articulating with a femoral component, the insert having a distal surface that fits against and moves on the proximal surface of the tray;

d) a generally vertical channel at the central portion of the insert that extends through the insert, the channel including an elongated slot portion that extends a partial distance through the insert, beginning at the distal surface of the insert and terminating at a position intermediate the proximal and distal surfaces of the insert, the slot extending generally along an anterior to posterior line;

c) the slot fitting the post, enabling a sliding action of the insert upon the tray; and f) a locking plug member for selectively locking the insert and tray together with a rotational connection, the plug member extending through the insert to connect with the post on the tray;

g) the plug being selectively attachable to the post or removable from the post, enabling selected relative motion between the insert and tray by respectively connecting or disconnecting the plug, wherein the insert is rotatable relative to the tray when the plug connects to the post; and h) the combination of the plug and slot defining a constraining mechanism that enables a number of different possible relative motions between the tibial insert and tibial tray including at least motion wherein the insert is selectively slidable and rotatable, or just rotatable relative to the tray when the plug is disconnected from the post.

16. The knee prosthesis of claim 15 wherein the post has a socket that receives the locking plug member.

17. The knee prosthesis of claim 15 wherein the slot extends completely through the insert, communicating with both the proximal and distal surfaces of the insert.

18. The knee prosthesis of claim 17 wherein the channel extends completely through the insert and the plug member extends through the insert at the proximal surface of the insert to connect with the post.

19. The knee prosthesis of claim 18 wherein the channel closely conforms to the locking plug at the proximal surface of the insert.

20. A knee prosthesis apparatus comprising:

a) a tibial component that includes a tibial tray portion adapted to be surgically implanted on a patient's transversely cut proximal tibia;

b) a post mounted at the central portion of the proximal surface of the tray, the post having a socket;

c) a tibial insert having an articulation surface for articulating with the femoral component, the insert having a distal surface that fits against and moves on the proximal surface of the tray;

d) a generally vertical channel at the central portion of the insert that extends through the insert, the channel including an elongated slot portion that extends a partial distance through the insert, beginning at the distal surface of the insert and terminating at a position intermediate the proximal and distal surfaces of the insert, the slot extending generally along all anterior to posterior line;

e) the slot registering upon and sliding with respect to the post of the tray; and f) a locking plug member for selectively locking the insert and tray together, the plug member extending through the insert to correct with the post on the tray enabling a rotational connection between the insert and tray;

g) means for providing selected relative motion between the insert and tray by respectively connecting or disconnecting the plug, wherein the insert is rotatable relative to the tray when the plug connects to the post; and h) wherein the insert is slidable and rotatable relative to the tray when the plug is disassembled from the post, wherein at least a portion of the slot extends through the insert, communicating with both the proximal and distal surfaces of the insert, wherein the slot has a larger transverse cross section at the distal surface of the insert and a smaller transverse cross section at the proximal surface of the insert.

* * * * *